US012599456B2

(12) United States Patent
Wells et al.

(10) Patent No.: US 12,599,456 B2
(45) Date of Patent: Apr. 14, 2026

(54) CAVITY SURGICAL LIGHTING APPARATUS

(71) Applicants:William Wells, Williamsburg, VA (US);
Gorav Ailawadi, Ann Arbor, MI (US)

(72) Inventors: William Wells, Williamsburg, VA (US);
Gorav Ailawadi, Ann Arbor, MI (US)

( * ) Notice: Subject to any disclaimer, the term of this
patent is extended or adjusted under 35
U.S.C. 154(b) by 465 days.

(21) Appl. No.: 18/082,638

(22) Filed: Feb. 1, 2023

(65) Prior Publication Data

US 2024/0252275 A1 Aug. 1, 2024

(51) Int. Cl.
*A61B 90/35* (2016.01)
*A61B 90/30* (2016.01)

(52) U.S. Cl.
CPC ........ *A61B 90/35* (2016.02); *A61B 2090/309*
(2016.02)

(58) Field of Classification Search
CPC .................. A61B 90/30–35; F21V 15/01–013
See application file for complete search history.

(56) References Cited

U.S. PATENT DOCUMENTS 9,727,080 B2 * 8/2017 Jung ..................... G06F 1/1652
2002/0141174 A1 * 10/2002 Parker .................. G02B 6/0038
362/330

2003/0095781 A1 * 5/2003 Williams ........... A61B 17/2812
385/901
2012/0149992 A1 * 6/2012 Duggal .............. A61B 17/0206
600/245
2012/0286680 A1 * 11/2012 Roberts .................. H05B 45/37
315/246
2016/0008088 A1 * 1/2016 Vayser ................... A61B 90/57
600/249
2016/0320027 A1 * 11/2016 Ito ......................... H05B 33/145
2016/0361133 A1 * 12/2016 Davis ................. A61B 17/3211
2017/0189133 A1 * 7/2017 Fox ............................ F21S 9/02
2017/0215717 A1 * 8/2017 Orringer .............. F21V 23/001
2017/0312045 A1 * 11/2017 McGuire ............... A61B 90/30
2018/0006249 A1 * 1/2018 Riedel ................. H10K 50/854
2018/0296203 A1 * 10/2018 Powley ............. A61B 17/0206
2019/0274716 A1 * 9/2019 Nott ..................... A61B 17/295
2020/0348009 A1 * 11/2020 Ansems ................ F21V 19/003
2023/0248465 A1 * 8/2023 Morgan ................. A61B 90/30
600/249

* cited by examiner

*Primary Examiner* — Eduardo C Robert
*Assistant Examiner* — Steven J Cotroneo

(57) ABSTRACT

The present invention comprises a flexible OLED lighting
panel for use in the medical field. The panel made of OLED
material powered by a small battery can be placed into a
surgical cavity for illuminating portions of the anatomy from
within the cavity. The housing for the panel includes a
malleable material that permits the panel to be bent or
otherwise configured to a shape that will best accommodate
the organs and other tissue defining the cavity. The battery,
switch, electronics and OLED material are a housed in a
single unit for ease of use during a procedure and disposal
afterward.

16 Claims, 2 Drawing Sheets

CAVITY SURGICAL LIGHTING APPARATUS

FIELD OF THE INVENTION

The present invention relates to a lighting apparatus for illuminating a surgical field that can be positioned in the surgical cavity at a location and depth chosen by the surgeon. More particularly, the apparatus is flexible and can be configured to adapt to the contours of the anatomy defining the cavity.

BACKGROUND

Lighting in the operating room of a hospital has traditionally been exterior to the surgical field. Located above the surgeons the lighting can illuminate the general area of interest, but falls short in many respects. As the surgeon and attendants are between the lighting and the patient, often shadows are cast which impair the surgeon's vision into certain parts of the cavity. Although many surgeons utilize headlights, they too have problems. That light is highly focused and illuminates only the specific area consistent with the position of the surgeon's sightline while other portions of the cavity remain obscured. Most lighting devices in the medical field generate an unacceptable level of heat that inhibits their use in close proximity to tissue. Otherwise the affected tissue can be damaged if subjected to the higher temperatures.

Traditional LED light panels have been utilized with retractors for location into parts of a surgical cavity. Such lighting is rigid and attached to the retractor paddles, denying the surgeon the flexibility and adjustment needed to achieve the desired illumination. Such devices are essentially fixed position devices and cannot be bent or configured to fit within the organs and other tissue defining cavity. Moreover, LEDs can generate excessive heat which can have an adverse effect on the surrounding tissue.

BRIEF SUMMARY OF THE INVENTION

The present invention comprises a flexible panel of lighting material that can be placed within a surgical cavity to enhance illumination of the surgical field. The panel can be in a multitude of sizes to so that it can accommodate any cavity regardless of size and depth. It is housed in a malleable material that will hold its shape in whatever configuration the surgeon specifies for a particular procedure. In the OLED panel described in detail below, all of the electronics, battery and OLED material can be housed in a single unit. This permits the entire device to be packaged in a sterile container and easily disposed of after use.

BRIEF DESCRIPTION OF THE DRAWINGS

Certain features of the invention are shown in drawings or otherwise in graphic form. The depiction of these features is of one embodiment only and should not be interpreted to limit the scope of the invention.

DETAILED DESCRIPTION OF THE INVENTION

Figures 1, 2:
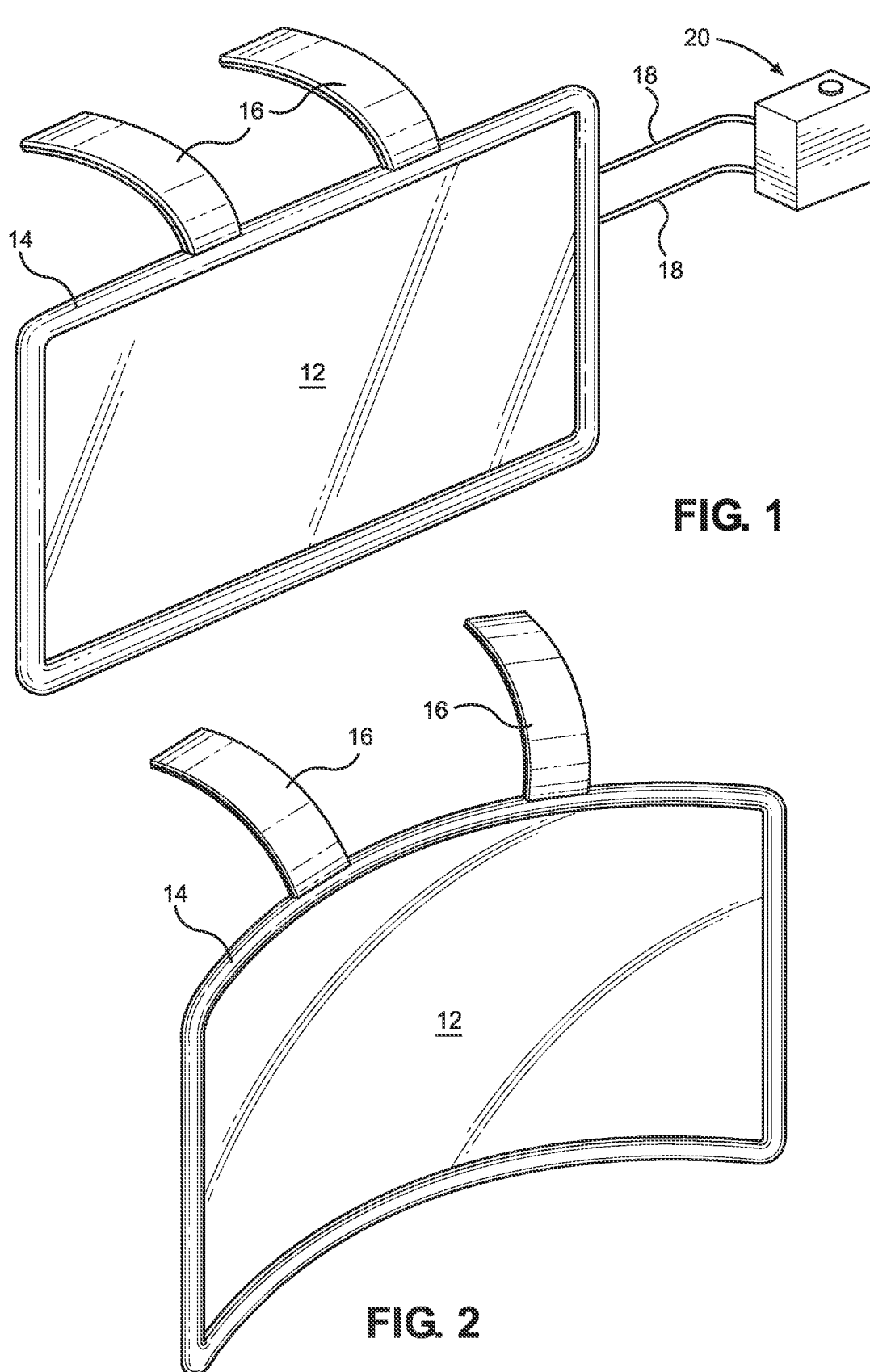
FIGS. 1 and 2 are perspective views of the OLED panel.
Figure 3:
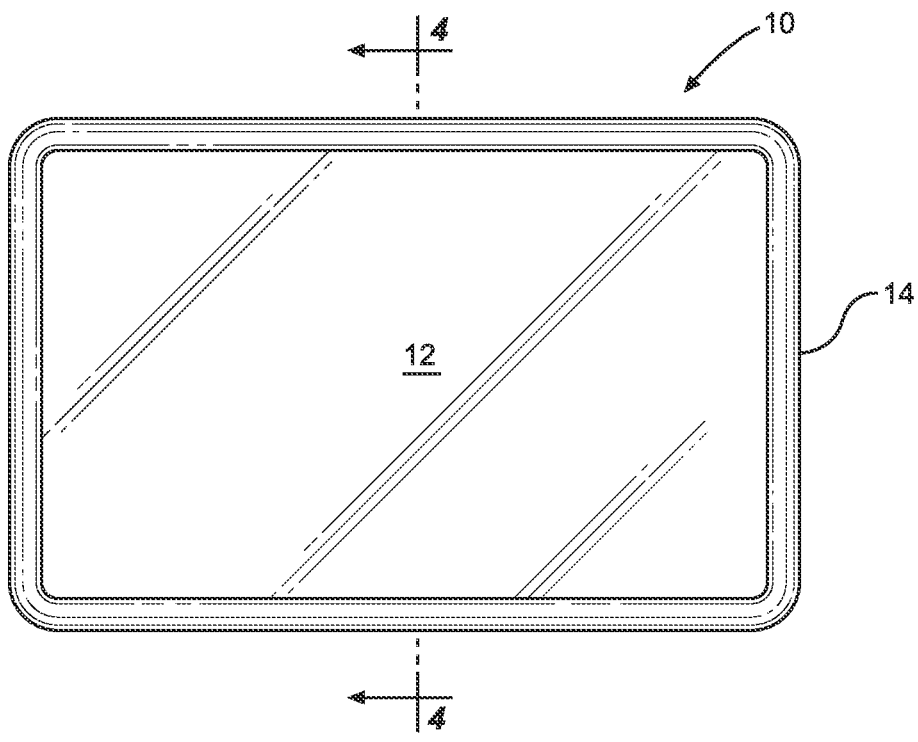
FIG. 3 is a plan view OLED panel.

The terms used herein are used to describe particular embodiments and should not be considered as limiting the full scope of the invention. The use of singular form in describing certain features should not be interpreted as excluding plural forms where appropriate. Unless otherwise defined all terms used to describe the invention have the meaning as understood by one of ordinary skill in the art. It should be understood that the meaning of terms herein to the extent defined in dictionaries and the like shall have the meaning that conforms to the context in which the term is found.

A problem for many surgeons is proper lighting for the surgical field, so that the relevant portion of the anatomy is adequately illuminated for a particular operation. Often the surgical cavity is small and relatively deep into the human anatomy making lighting more difficult. Although this minimal intrusion is an advantage for the safety and quick recovery for the patient, it creates illumination problems for the surgeon. General overhead lighting can create shadows that hide portions of the organ or other tissue. Head lamps are not the total solution, as they employ a highly focused beam of light that is not necessarily consistent with illuminating an area of interest to the surgeon. In certain procedures internal lighting of the field would be helpful as a complement to these traditional lighting methods.

The invention described herein overcomes many of these problems. A battery operated, thin, flexible and adjustable lighting device that can actually be inserted into the cavity can provide illumination to the portions of the field that previously were obscured. Because they can be made of plastic material, OLEDs are especially desirable type of lighting for this purpose. The flexible character of the material enables it to be bent into a shape to fit the cavity as needed by the surgeon. OLEDs generate almost no heat thus eliminating the need for heat sinking that other lighting such as LEDs require. The entire apparatus may be of a size and weight so that it does not interfere with the traditional surgical techniques. As a result it can come in contact with tissue without adverse effect.

The nature of the light for OLED panel is one where the light is dispersed evenly over the full length and width of the entire emissive surface without the need for lenses or reflectors. The light itself is of a warm pleasant character without glare, thus minimizing shadow effects that would be problematic for e surgeon. The panel's location can be adjusted within the cavity to produce the maximum illumination required. Because the OLED is so incredibly thin, it takes up almost no space in surgical cavity making its insertion and removal a relatively easy matter without affecting surrounding organs.

The entire OLED panel with electronics and battery can be packaged in sterile form to insulate the patient from dangerous pathogens, as is typical for instruments and the like used in the operating room. The panel is housed or otherwise designed to maintain its configuration, once bent into the form desired. Thus, the surgeon has the option of configuring and reconfiguring the panel to conform to the relevant portion of the anatomy. In this manner the surgeon has complete control of how the field is illuminated rather than relying on fixed apparatus.

An embodiment of the invention provides for an apparatus including an organic light emitting diode (OLED) 12, a battery connected to the OLED, and a switch electrically connected between the battery and the OLED, wherein the switch can control or toggle the OLED between an on and off position. The switch, battery and electronics are housed in battery housing 20 connected by hard wires to OLED panel 12. The apparatus may also include a fastener 16 to removably secure the OLED material to a surface near an area to be subjected to light emitted by the OLED material. The battery may be removable from the apparatus for replacement or recharging. It is preferred however, that the apparatus be disposable as an entire unit after a single use in a medical procedure.

An adjustable securing mechanism 16 may be integrated with the OLED panel, permitting it to be fixed to a surface near the area to be illuminated. Part of this embodiment may include a battery compartment with the switch electrically connected thereto from a remote position. Once attached to the desired surface, the switch may control power to the OLED material from the battery. This approach permits the OLED panel to be moved, adjusted, lowered or raised without necessarily changing the switch location.

A preferred embodiment includes a kit for installing an OLED fixture, including an OLED panel, a battery, a switch, and a securing mechanism. The attachment system permits the panel to be attached to the flat surfaces of larger instruments such as right angle sternal retractors or smaller self-retaining retractors with arms connected to a pivot with a paddle assembly. Or, it can be attached directly to any surface adjacent the surgical cavity.

The mechanism described above for attaching an OLED strip to a surface is not limited to a particular fastener. Exemplary securing mechanisms can include bendable tines or flanges, snap fasteners, hooks, tines and/or adhesives. Various adhesives can be used between the substrate and the surface in lieu of hooks, tines, flanges and the like. Such adhesives can be permanent or temporary. As the surface to which the OLED can be affixed may not be rigid, such as surrounding epidermis or an adhesive surgical drape, the attaching mechanism includes flanges with an adhesive on one surface facing the element it will be attached to. The adhesive is sufficient to secure the panel in place while permitting it to be removed and re-attached if necessary to accommodate the surgeon.

Embodiments can also involve a method in which an activation event is wirelessly detected. For such connection, the activation of the power source may be made through radio frequency, audio frequency, infrared or other light frequency. With this system the activation apparatus can be located more remote from the OLED light apparatus itself in a manner that is more convenient to the surgeon.

For uses where weight and size are a premium, both the switch and battery should be relatively small. The panel is exceptionally thin permitting it to be inserted into the cavity essentially taking up almost no space. The depth dimensions of the OLED material strip and switch may be less than 2 mm. The battery may be relatively thin as well as having a diameter of 22 mm and a thickness of 3.2 mm. The dimensions of the battery and switch can be larger and still have the advantages of the invention depending on the particular operation. The weight of the battery is about 2.9 g and can range between less than 1.5 g to about 10 g or larger. The switch may weigh about 3.2 g and can range between 2.0 and 10 g and larger.

The switch may be pressure actuated that enables the user to depress the outer surface thereof to turn the light on and again to turn it off. Other types of switches could be used such as a touch switch, toggle switch, or the like. Although the switch is typically electrically hard wired connected between the battery and the OLED material in close proximity, it could be located elsewhere so long as it is in a circuit that controls power to the OLED material.

Examples of other switches that may be used include membrane type switches, optical switches, rocker switches, coded DIP switches, and snap-action switches. The touch switch can be a capacitance or a resistance type which relies on the change of resistance or capacitance caused by the touch of the human finger for example. Such switches come in various sizes to comply with the electronic requirements as well as the size specifications to fit in the environment where the apparatus will be used. An advantage of a touch switch may include that it can be sealed to avoid fluids and other debris that could otherwise hamper its operation.

OLEDs are dimmable similar to that of LEDs or other types of lighting. With the OLED panel the dimming feature is accomplished by controlling the current delivered to the device. This is typically done by adopting a driver circuit that permits dimming of the OLED panel as well as providing the necessary voltage to operate the light. Thus the surgeon can control the intensity of illumination for the field of surgery.

The battery employed may be rechargeable, can be removed from the panel and charged as needed. Batteries that can be used for this purpose include Nickel Cadmium, Nickel Metal Hydride or any other battery that can be recharged upon depletion. Non-rechargeable batteries can be used as well such as alkali batteries and non-rechargeable Lithium batteries. The battery should preferably be matched to the OLED material to produce the desired amount of illumination to the surgical cavity.

The type of light preferred can be selected by the surgeon as well. OLEDs can produce light in the range between warm or soft light at 2700K and a more neutral or blue light of 4000K. This gives the surgeon the option to choose which light works best for a particular procedure. Some surgeons may simply have a preference for a certain type of light from a personal perspective.

As OLEDs do not need much power, a battery can operate between about 3 and 6 volts and preferably between 3.6 and 4.8 volts. For example, a battery for operating the OLED material can be a CR2032 button type battery that is generally available. Another type of battery is a Li-ion Any battery will suffice so long as it produces enough voltage to generate a current in the OLED to provide the desired amount of light without harming the OLED. It is preferable that the battery last a reasonable time before it must be replaced or recharged. For the use described herein the battery should be relatively small and thin to minimize space requirements.

For recharging the battery, if needed before use, conventional recharging devices can be used so long as they are compatible with the batteries used in the invention. Particularly because the batteries use so little power, portable devices such as solar chargers can be used to recharge the batteries once depleted.

The OLED material is practically unlimited in the shape or form it can take for lighting in various types of surgical procedures. For example open heart surgery will probably require larger panels compared to other minimally invasive procedures where smaller incisions are made. A feature of OLED material is that it can be cut to the desired size and form and still operate properly. Combined with flexibility, the OLED panel can fit in any surgical cavity and illuminate the portion needed by the surgeon.

The OLED panel is housed in a malleable structure that permits the panel to be bent and otherwise configured to the form desired by the surgeon. This usually comprises a metal or plastic tube or rod portion 14 affixed to the perimeter of the panel. It can be aluminum, steel, copper or other similar material. It must be an inelastic, ductile material (plastic) that can be permanently deformed at room temperature and hold the panel into the form bent by the surgeon. The

Figure 4:
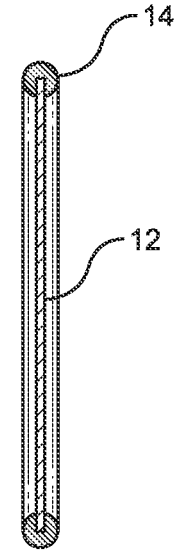
FIG. 4 is a cross-sectional view of the OLED panel.

5 exposed portion of the housing should have a bull nose, arcuate shape to prevent the edges from cutting into or otherwise damaging the adjacent tissue. See FIG. 4. The radius of curvature for the bull nose can range between 2.5 and 5.0 mm and larger for certain uses.

The entire package for the OLED panel can be sterilized for use in the operating room. Since the battery, electronics and OLED material can be arranged in a single housing completely insulated from the atmosphere, it can be sterilized as a single unit before being packaged. If a design is adopted that has some parts exposed independently of others, it may be necessary to sterilize them separately. An alternative is to seal the housing and the lighting elements of the invention with plastic or other material that will permit it to be sterilized without affecting the lighting characteristics.

After a sterilization step the panel is packaged in a sterile container as is typically done. The package can then be opened in the OR as needed without any additional effort required by the surgeon for its use. The panel is simply removed from its package and placed in the surgical field as desired. After use, it can be disposed of as with any other potentially hazardous material would be.

Those skilled in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited. Other modifications will become apparent to the skilled practitioner upon a study of the drawings, specification, and following claims. Features of certain embodiments may be combined with other features from the other embodiments. Thus, the embodiments should not be seen as mutually exclusive or limiting in any way.

What is claimed is:

1. A medical lighting apparatus comprising:
a. a light emitting panel including an organic light emitting diode (OLED) material sized for insertion into an anatomical surgical cavity to illuminate the surgical field independently of any retractor blade or other surgical instrument;
b. the OLED material being made of a flexible material of less than 5 mm in thickness to permit it to be bent into the desired shape for the surgeon's needs;
c. a housing for the panel made of malleable material that permits the panel to retain the form into which it can be bent;
d. a battery having a thickness of 5 mm or less and at least one of a width and length dimension of 22 mm or less;
e. the battery being electrically connected to the OLED material;
f. a switch for controlling power from the battery to the OLED material; and
g. the housing having a thickness of between 5-10 mm.

2. The apparatus according to claim 1 wherein the battery has a diameter of 22 mm and thickness of 3.2 mm.

3. The apparatus according to claim 1 wherein the weight of the battery ranges between 1.5 g to 10 g.

4. The apparatus according to claim 1 wherein the weight of the switch ranges between 3 g and 10 g.

5. The apparatus according to claim 1 wherein the switch is integral with the housing for the panel.

6. The apparatus according to claim 1 wherein the switch is separable from the housing and operable remotely therefrom.

7. The apparatus according to claim 6 wherein the switch is wirelessly connected to said panel for activating the OLED material between an "on" and an "off" position.

8. The apparatus according to claim 6 wherein the switch includes a driver circuit that permits dimming of the light generated by the OLED material.

9. The apparatus according to claim 1 wherein the battery is operable between 3 and 6 volts.

10. A medical lighting apparatus comprising:
a. a light emitting panel including an organic light emitting diode (OLED) material sized for insertion into an anatomical surgical cavity to illuminate the surgical field independently of any retractor blade or other surgical instrument, the panel being rectangular in shape;
b. the OLED material being made of a flexible material of less than 3 mm in thickness to permit it to be bent into the desired shape for the surgeon's needs;
c. a housing for the lighting panel made of a malleable material that permits the panel to retain the form into which it can be bent, the housing including a tubular ductile material surrounding the panel;
d. a battery having a thickness of 5 mm or less and at least one of a width and length dimension of 22 mm or less;
e. the battery being electrically connected to the OLED material;
f. a switch for controlling power from battery to the OLED material; and
g. the panel, the housing, the switch and the battery being integrated into a single unit for insertion into a surgical cavity.

11. The apparatus according to claim 10 wherein the single unit is made of sterilizable material.

12. The apparatus according to claim 10 further comprising a securing mechanism for securing the panel to a surface adjacent the surgical cavity.

13. The apparatus according to claim 10 wherein the battery is wirelessly connected to the panel.

14. A medical lighting apparatus comprising:
a. A light emitting panel including an organic light emitting diode (OLED) material sized for insertion into an anatomical surgical cavity to illuminate the surgical field independently of any retractor blade or other surgical instrument;
b. the OLED material being made of a flexible material to permit it to be bent into the desired shape for the surgeon's needs;
c. the panel including a housing made of malleable material that permits the panel to retain the form into which it was bent;
d. the housing having a thickness of 10 mm or less;
e. the housing surrounding the perimeter of the OLED material;
f. a battery electrically connected to the OLED material;
g. a switch for controlling power from the battery to the OLED material;
h. the battery and the switch having a thickness of 10 mm or less; and
i. the light emitting panel, the battery and the switch being packaged in a sterile container.

15. The apparatus according to claim 14 wherein said malleable material affixed to the perimeter of the panel includes an arcuate cross-sectional portion on its outermost perimeter.

16. The medical lighting apparatus according to claim 14 wherein the panel, the OLED material, the battery, and the switch and housing are combined in a single unit.

\* \* \* \* \*